United States Patent [19]
Wallace

[11] 4,298,693
[45] Nov. 3, 1981

[54] FERMENTATION APPARATUS

[76] Inventor: Michael W. Wallace, Rt. 2, Box 53, Dustin, Okla. 74839

[21] Appl. No.: 173,356

[22] Filed: Jul. 29, 1980

[51] Int. Cl.³ .......................... C12M 1/02; C12M 1/12
[52] U.S. Cl. ..................................... 435/305; 435/311; 435/315; 435/316
[58] Field of Search ............................... 435/302–304, 435/305–308, 311, 315, 316, 161, 162; 203/DIG. 13, 19, DIG. 23

[56] References Cited
FOREIGN PATENT DOCUMENTS
2405993  6/1979  France .................................. 203/19

OTHER PUBLICATIONS
Margaritis et al., "The Rotorfermenter II, Application to Ethanol Fermentation"; Biotech., & Bioeng., vol. 20, pp. 727–753 (1978).
Biotech. & Bioeng., vol. 20, pp. 709–726 (1978).
Biotech. & Bioeng., vol. 21, pp. 2203–2223 (1979).

*Primary Examiner*—Benoit Castel
*Attorney, Agent, or Firm*—Dunlap, Codding & McCarthy

[57] ABSTRACT

A fermentation apparatus for converting agricultural raw materials into a fermented liquor containing about 10 weight percent ethanol comprising a fermentation chamber, a separation chamber, a conduit for transporting mash through the fermentation chamber and the separation chamber, and at least one pump for circulating an aqueous yeast-containing solution in the fermentation chamber into the conduit for contact with the mash to convert the simple sugars in the mash to ethanol. A gas separator is positioned within the separation chamber to remove the carbon dioxide generated by the fermentation of the simple sugars in the mash such that the carbon dioxide does not enter and agitate the aqueous ethanol mixture in the separation chamber.

33 Claims, 6 Drawing Figures

FERMENTATION APPARATUS

BACKGROUND OF THE INVENTION

1. Field of the Invention

This invention relates generally to the field of fermentation, and more particularly, but not by way of limitation, to a fermentation apparatus for continuously converting agricultural raw materials into a fermented liquor.

2. Description of the Prior Art

The fermentation of agricultural raw materials to produce ethanol is well known. The production of ethanol from agricultural raw materials, such as corn, wheat, sugar cane, potatoes, beets, Jerusalem artichokes, and the like, has recently become of great importance in the United States as a source of liquid fuel.

In the past foreign crude oil has provided the raw materials for about one-half of the liquid fuels consumed in the United States. However, with the recent instabilities in many of the foreign oil producing countries the cost of the foreign produced crude oil, as well as the uncertainty of the supply of the crude oil, has resulted in the direct efforts to reduce the dependency of the United States on foreign crude oil as the primary source for liquid fuels.

Ethanol is a liquid fuel that can substitute domestic renewable resources for petroleum products now and in the years to come. Fermentation ethanol, a nonpetroleum fuel, is attaining widespread use in the United States in the form of gasohol, a blend of ten percent agriculturally derived anhydrous ethanol and ninety percent unleaded gasoline.

Ethanol can be made by the fermentation process from three types of agricultural raw materials, namely saccharines (materials in which the carbohydrate is present in the form of simple, directly fermentable sugars containing 6 and 12 carbon atoms, such as glucose, fructose, and maltose), starchy materials (materials containing more complex carbohydrates such as starch and inulin that can be broken down into simple sugars containing 6 and 12 carbon atoms by hydrolysis with a weak acid or by the action of enzymes in a process called malting), and cellulose materials (materials containing cellulose that can be hydrolyzed with an acid into fermentable sugars).

The production of ethanol by fermentation techniques has been known for many years. Basically, fermentation is a process in which microorganisms, such as yeast, convert the simple sugars of mash into ethanol and carbon dioxide. The agricultural raw material employed in the fermentation process, as well as the process steps required to convert the carbohydrates, starchy materials, or cellulose materials of the agricultural raw materials into the sample, directly fermentable sugars containing 6 and 12 carbon atoms, (i.e., glucose, fructose, and maltose), can vary widely and will be dependent upon the particular agricultural product employed as the raw material in the fermentation process.

The fermented liquor (i.e., beer) resulting from the fermentation of the fermentable sugars in the mash is generally an aqueous solution containing about ten weight percent ethanol. The fermented liquor is then distilled to obtain the anhydrous ethanol for use as a fluid fuel.

While the fermentation of agricultural products as described above has been known for many years, the fermentation apparatus used in carrying out the fermentation have generally been batched reactors or complicated, expensive continuous reactors. While such reactors, whether batched or continuous fermentation reactors have met with success, a need has now arisen for an improved fermentation apparatus which will enable one to employ flow processing techniques in the production of ethanol from agricultural products which is inexpensive, simple in construction, and efficient in operation. However, such a fermentation apparatus must be capable of economically producing ethanol from the agricultural products using conventional yeast materials.

SUMMARY OF THE INVENTION

Therefore, an object of the present invention is to provide a proved fermentation apparatus for converting fermentable sugars of agricultural raw materials into ethanol.

Another object of the invention is to provide an improved fermentation apparatus using flow processing techniques which can be employed in a continuous fermentation process to effectively and efficiently convert the fermentable sugars of agricultural raw materials into ethanol.

Yet another object of the present invention is to provide an improved fermentation apparatus which is simple in design, economical in construction, and cost effective for fermenting grain mash (both in solid and liquid form, simultaneously) to produce ethanol.

These and other objects, advantages, and features of the present invention will readily be apparent to those skilled in the fermentation art from a reading of the following detailed description, drawings, and the appended claims.

According to the present invention an improved fermentation apparatus is provided for the continuous fermentation of simple sugars (i.e., sugars containing 6 and 12 carbon atoms) derived from agricultural raw materials to produce ethanol. Broadly, the fermentation apparatus cmprises a fermentation chamber, a separation chamber, and a conduit for conveying the fermentable mash through the fermentation chamber and the separation chamber. The separation chamber is operably connected to, and in fluid communication, with the fermentation chamber such that the separation chamber is vertically disposed and the elongated axis of the separation chamber is substantially normal to the elongated axis of the fermentation chamber. The mash containing conduit is constructed so that the fermentable mash being transported therethrough is retained in the conduit and a yeast-containing slurry in the fermentation chamber can be circulated into the conduit for contact with the fermentable mash. A gas separating assembly is positioned within the separation chamber of the fermentation apparatus, the gas separating assembly being adapted to remove the carbon dioxide generated by the fermentation of the mash and thus prevent the carbon dioxide from entering and agitating the aqueous ethanol mixture in the separation chamber.

DESCRIPTION OF PREFERRED EMBODIMENTS

Referring to the drawing, and particularly to FIGS. 1, 2, 3, and 4, shown therein and designated by the reference numeral 10 is an improved fermentation apparatus constructed in accordance with the present invention. The fermentation apparatus 10 is adapted to be used in a continuous flow process for converting the simple sugars of a fermentable mash (i.e., a mash which has been processed such that the carbohydates in the mash have been broken down to sugars containing 6 to 12 carbon atoms, such as glucose, fructose, and maltose) to ethanol. The fermentation apparatus 10 comprises a substantially horizontally disposed fermentation chamber 12, a substantially vertically disposed separation chamber 14, and a conduit 16 disposed within and extending through the fermentation chamber 12 and the separation chamber 14.

The fermentation chamber 12, an elongated housing adapted to receive and containing slurry therein, is provided with an open first end 18 and a closed second end 20. The separation chamber 14, also illustrated as an elongated housing and adapted to receive and separate particulate matter in the beer produced by the fermentation of the mash and the yeast containing slurry in the fermentation chamber 12, is provided with a closed upper or first end 22 and an open lower or second end 24. Thus, in an assembled position the open lower end 24 of the separation chamber 14 is disposed adjacent the open first end 18 of the fermentation 12 such that the fermentation chamber 12 is in fluid communication with the separation chamber 14.

The fermentation chamber 12 of the fermentation apparatus 10 comprises a first sidewall 26, a spatially disposed second sidewall 28, an upper wall 30, a spatially disposed lower wall 32, and an end wall 34. The first and second sidewalls 26, 28 are positioned between and connected to the upper wall 30 and the lower wall 32, and each of the walls 28, 30, 32 and 34 are connected to the end wall 34 such that a fluid passageway 36 is formed. The first sidewall 26 of the fermentation chamber 12 diverges from the second sidewall 28, and the upper wall 30 of the fermentation chamber 12 diverges from the lower wall 32 so that the flow rate of the yeast containing slurry in the fluid passageway 36 of the fermentation chamber 12 decreases as a function of the distance from the closed second end 20 of the fermentation chamber 12 to the open first end 18 thereof.

The separation chamber 14 of the fermentation apparatus 10 comprises a first sidewall 38, a spatially disposed second sidewall 40, a front wall 42, a spatially disposed rear wall 44, and an end wall 46. The first and second sidewalls 38, 40 are positioned between and connected to the front wall 42 and the rear wall 44, and each of the walls 38, 40, 42 and 44 are connected to the end wall 46 such that a fluid passageway 48 is formed. The front and rear walls 42, 44 of the fermentation chamber 12 converge from the end wall 46 of the separation chamber 14 substantially as shown. Thus, the rate of flow of the liquid through the fluid passageway 48 of the separation chamber 14 decreases as a function of the distance from the open second end 24 of the separation chamber 14 to the closed first end 22 thereof.

In an assembled position of the fermentation chamber 12 and the separation chamber 14, the first and second sidewalls 38, 40 of the separation chamber 14 are disposed adjacent the open first end 18 of the fermentation chamber 12 and connected to the first and second sidewalls 26, 28 of the fermentation chamber 12, the front wall 42 of the separation chamber 14 is operably connected via a connecting assembly 50 to the upper wall 30 of the fermentation chamber 12, and the rear wall 44 of the separation chamber 14 is connected to the lower wall 32 of the fermentation chamber 12. Thus, the separation chamber 14 vertically extends from the open first end 18 of the fermentation chamber 12 such that the central elongated axis of the separation chamber 14 is substantially normal to the central elongated axis of the fermentation chamber 12 and the fluid passageways 36, 48 of the fermentation chamber 12 and the separation chamber 14, respectively, openly communicate one with the other.

The fermentation chamber 12 is further provided with a centrally disposed first opening 52 and a second opening 54 in the end wall 34; and the separation chamber is provided with a centrally disposed opening 56 in the end wall 46. The conduit 16 is disposed through the first opening 52 of the end wall 34 of the fermentation chamber 12 and the opening 56 in the end wall 46 of the separation chamber 14, and the conduit 16 is connected to the end walls 34, 46 in a fluidtight relationship such that a medial portion 56 of the conduit 16 extends between the end walls 34, 46 and thus through the fluid passageways 36, 48 of the fermentation chamber 12 and the separation chamber 14.

A conduit 60 is disposed through the second opening 54 in the end wall 34 of the fermentation chamber so as to be in fluid communication with the fluid passageway 36 of the fermentation chamber 12. The conduit 60 establishes fluid communication between an aqueous supply vessel (see FIG. 5) and the fluid passageway 36 of the fermentation chamber 12 so that water (and additional amounts of yeast when same are determined necessary) can be directed into the fermentation chamber 12, and thus into the separation chamber 14, of the fermentation apparatus 10. Water or an aqueous yeast slurry can be constantly supplied to the fermentation chamber 12 to insure that the yeast concentration therein is maintained at a proper level during the fermentation of the simple sugars of the fermentable mash, and to maintain a proper liquid level in both the fermentation chamber 12 and the separation chamber 14 of the fermentation apparatus 10.

Figure 5:
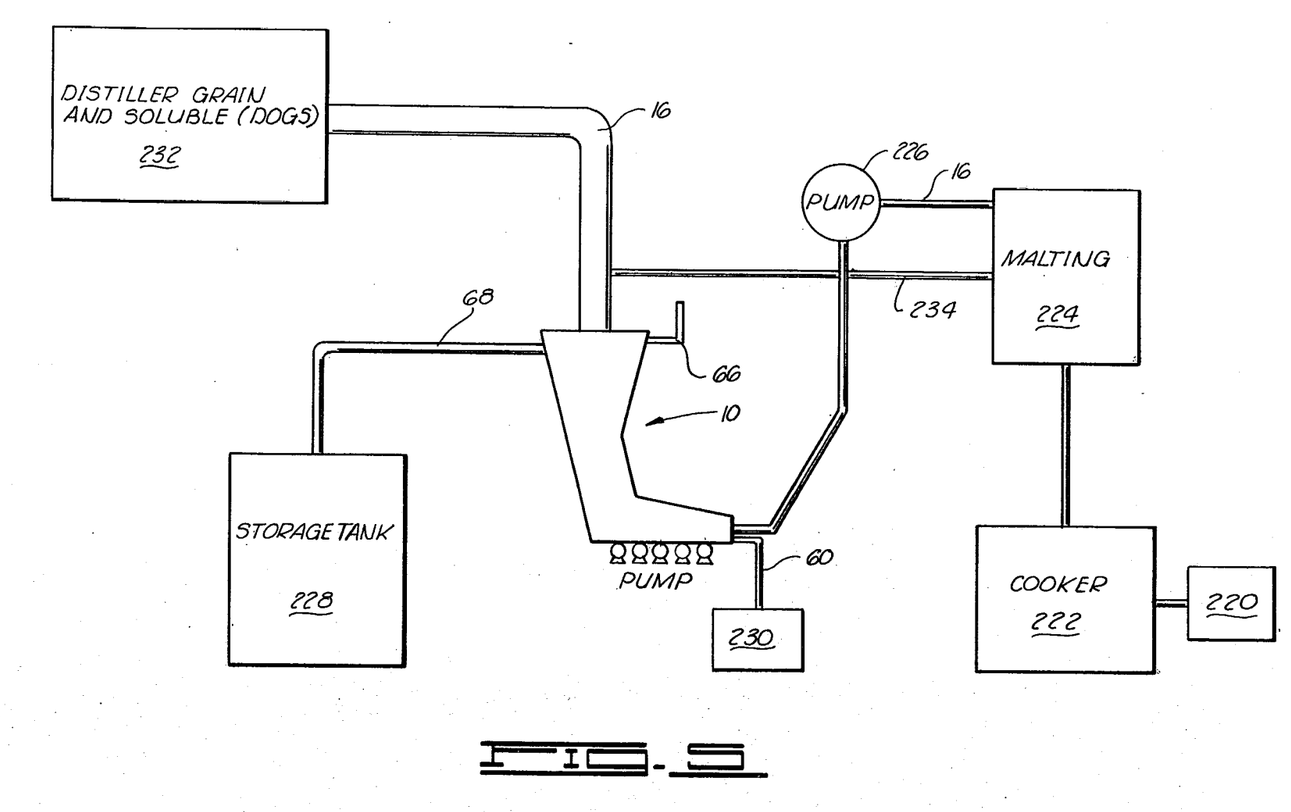
FIG. 5 is a diagrammatic representation of a continuous fermentation process utilizing the improved fermentation apparatus of the present invention.

The front wall 42 of the separation chamber 14 is provided with an opening 62, the opening 62 being positioned in close proximity to the end wall 46 of the separation chamber 14. The rear wall 44 of the separation chamber 14 is also provided with an opening 64, the opening 64 being positioned a greater distance from the end wall 46 of the separation chamber 14 than the distance between the opening 62 in the front wall 42 of the separation chamber 14. A conduit 66 is positioned through the opening 62 in the front wall 42 of the separation chamber 14; and a conduit 68 is positioned through the opening 64 in the rear wall 44 of the separation chamber 14. The conduit 66, which openly communicates with the passageway 48 of the separation chamber 14, allows one to vent the carbon dioxide generated by fermentation of the mash; whereas the conduit 68, which also openly communicates with the passageway 48 of the fermentation chamber 12, enables the beer formed by the fermentation of the mash to be continuously withdrawn from the separation chamber 14 and directed to a still (not shown) or a holding vessel (as illustrated in FIG. 5.)

Figures 1, 2:
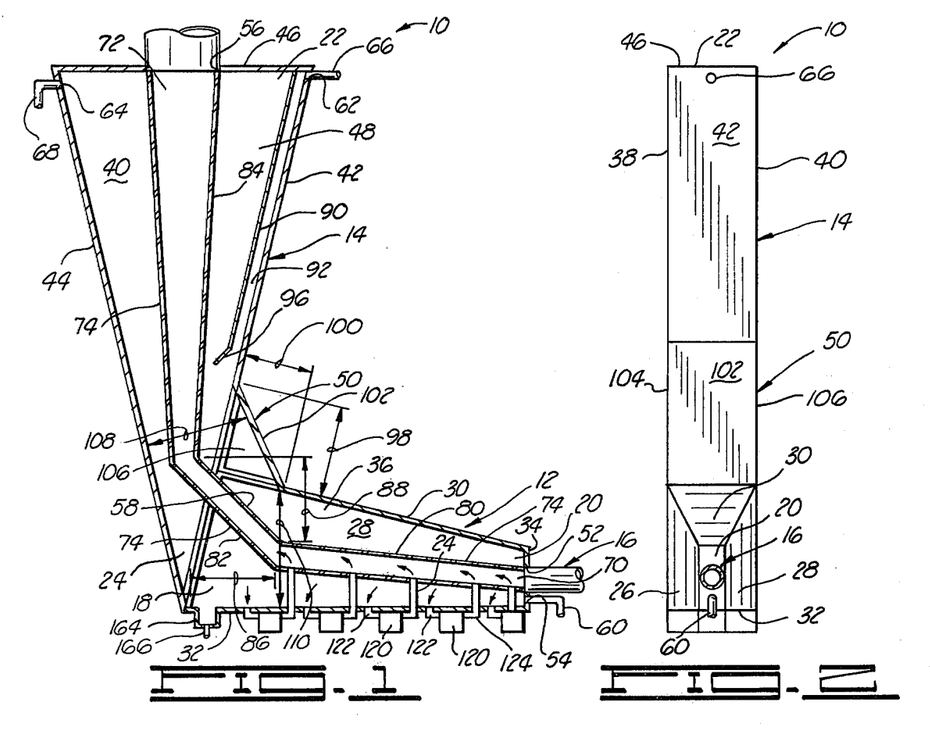
FIG. 1 is a partially broken cross-sectional view of the improved fermentation apparatus of the present invention.
FIG. 2 is a front elevational view of the improved fermentation apparatus of FIG. 1.

The conduit 16 of the fermentation apparatus 10 is provided with a first end portion 70, the medial portion 58, and a second end portion 72. The medial portion 58 of the conduit 16 is fluid permeable so that the yeast in the aqueous slurry in the fluid passageway 36 of the fermentation chamber 12 can be circulated into the medial portion 58 of the conduit 16 and contacted with the fermentable mash being moved through the conduit 16. In order the desired fluid permeability in the medial portion 58 of the conduit 16, a plurality of apertures 74 can be disposed through the medial portion 58 of the conduit 16 as illustrated in FIG. 1, or the conduit 16 can be formed of any suitable liquid permeable material, such as a mesh material, a fluid permeable membrane, and the like. However, in forming the medial portion 58 of the conduit 16 care must be exercised to insure that the apertures 74, or openings in the mesh material are of a size to prevent any substantial portion of the mash moving through the conduit 16 from exiting the conduit 16 through the apertures 74 in the medial portion 58 of the conduit 16, or the openings in the mesh material. By constructing the conduit 16 in the matter described, the yeast-containing slurry can be contacted with the mash in the medial portion 58 of the conduit 16 so that fermentation of the mash occurs in the medial portion 58 of the conduit 16. When confining the fermentation of the mash in the medial portion 58 of the conduit 16 one can substantially reduce the amount of suspended solids in the beer in the separation chamber 14 resulting from the fermentation of the mash, while at the same time simply and efficiently carrying out a continuous fermentation process.

As previously stated, and as shown in the drawings, the medial portion 58 of the conduit 16 extends through the fluid passageway 36 of the fermentation chamber 12 and the fluid passageway 48 of the separation chamber 14. The medial portion 58 of the conduit 16 is characterized as having a first section 80, a second section 82, and a third section 84. The first section 80 of the medial portion 58 of the conduit 16 extends from the end wall 34 of the fermentation chamber 12 and terminates a distance 86 from the open first end 18 of the fermentation chamber 12. Further, the first section 80 of the medial portion 58 of the conduit 16 is disposed in the fluid passageway 36 of the fermentation chamber 12 such that the first section is upwardly inclined as same extends from the end wall 34 of the fermentation chamber 12 in the direction of the open first end 18 of the fermentation chamber 12.

The third section 84 of the medial portion 58 of the conduit 16 extends from the end wall 46 of the separation chamber 14 and terminates a distance 88 from the first section 80 of the medial portion 58 of the conduit 16. Further, the third section 84 of the medial portion 58 of the conduit 16 is disposed so as to be in an offset relationship with the first section 80 of the medial portion 58 of the conduit 16. The third section 84 of the medial portion 58 of the conduit 16 is substantially vertically disposed in the fluid passageway 48 of the separation chamber 14 and the walls of the third section 84 of the medial portion 58 of the conduit 16 diverge as the third section 84 extends in the direction of the end wall 46 of the separation chamber 14 substantially as shown in the drawings. Thus, the flow rate of the mash through the third section 84 of the medial portion 58 of the conduit 16 decreases as a function of the length of the third section 84.

The second section 82 of the medial portion 58 of the conduit 16 extends between the fluid passageways 36, 48 of the fermentation chamber 12 and the separation chamber 14 and interconnects the first and third sections 80, 84 of the medial portion 58 of the conduit 16. The unique construction and interconnection of the first section 80, the second section 82, and the third section 84 of the medial portion 58 of the conduit 16, as shown in the drawings, (including the angular disposition of each of the before-mentioned sections with one another and with the fluid passageways 36, 48 of the fermentation and separation chambers 12, 14, respectively) cooperate to assist in the movement of the mash therethrough and improve the efficiency and operation of the fermentation apparatus 10.

In order to collect and separate the carbon dioxide generated in the fermentation chamber 12 of the fermentation apparatus 10 by the conversion of the simple sugars in the mash by the yeast, a gas separating plate 90 is connected to the end wall 46 of the separation chamber 14 such that the plate 90 extends along the front wall 42 of the separation chamber 14 and forms a passageway 92 therebetween. The plate 90 is disposed between the first and second side walls 38, 40 of the separation chamber 14 and secured thereto so that carbon dioxide entering the passageway 92 is directed through the passageway 92 and exits the separation chamber 14 via the opening 62 in the front wall 42 of the separation chamber 14 and the conduit 66. A valve 94 is operably connected to the conduit 66 to control the rate of flow of the carbon dioxide through the passageway 92, the conduit 66, and thus facilitate the control of the fermentation process being carried out in the fermentation apparatus 10. It should be noted that the plate 90 and the front wall 42 of the separation chamber 14 substantially prevent the carbon dioxide from agitating the beer in the separation chamber 14 and thus facilitates in the separation of particulate matter from the beer.

In order to assist in directing the carbon dioxide into the passageway 92 a lower end 96 of the plate 90 is flared in a direction away from the front wall 42 of the separation chamber 14 substantially as shown in the drawings. Further, in order to further assist the direction of the carbon dioxide into the passageway 92 formed between the plate 90 and the front wall 42 of the separation chamber 14, the front wall 42 terminates a distance 98 from the upper wall 30 of the fermentation chamber 14, and the upper wall 30 of the fermentation chamber 12 terminates a distance 100 from the front wall 42 of the separation chamber 14. The connecting assembly 50, which interconnects the adjacently disposed end portions of the upper wall 30 of the fermentation chamber 12 and the front wall 42 of the separation chamber 14, comprises a connecting plate 102, a first side connecting plate 104, and a second side connecting plate 106. The connecting plate 102 is disposed between and connected to the upper wall 30 of the fermentation chamber 12 and the front wall 42 of the separation chamber 14 such that the plane of the connecting plate 102 is substantially parallel to the plane of the rear wall 44 of the separation chamber 14, and a distance 108 between the connecting plate 102 and the rear wall 44 of the separation chamber 14 is substantially equal to a distance 110 between the upper wall 30 and the lower wall 32 of the fermentation chamber 12 at the position of attachment of the connecting plate 102 to the upper wall 30 of the fermentation chamber 12.

The first side connecting plate 104 is positioned between the connecting plate 102 and the first side wall 38 of the separation chamber 14, and the second side connecting plate 106 is positioned between and connected to the connecting plate 102 and the second side wall 40 of the separation chamber 14. Thus, the connecting plate 102, the first side connecting plate 104, and the second side connecting plate 106 cooperate with the lower end 96 of the plate 90 to form a funnel surface for directing the carbon dioxide generated during the fermentation of the mash into the passageway 92.

In order to insure that the yeast slurry in the fermentation chamber 12 of the fermentation apparatus 10 contacts the fermentable mash in the medial portion 58 of the conduit 16, a plurality of pumps 120 are mounted on the lower wall 32 of the fermentation chamber 12. Each of the pumps 120 is in fluid communication with the aqueous yeast slurry in the fermentation chamber 12 via a conduit 122 and each of the pumps 120 circulate the aqueous yeast slurry into the first section 80 of the medial portion 58 of the conduit 16 via a conduit 124. The pumps 120 (five being depicted) are variable speed recirculating pumps adapted to continuously circulate the yeast slurry in the fermentation chamber 12 into the first section 80 of the medial portion 58 of the conduit 16 so that the yeast slurry contacts the fermentable mash passing through the conduit 16. By injecting the yeast slurry directly into the first section 80 of the medial portion 58 of the conduit 16 the fermentable sugars in the mash are contacted with the yeast in the yeast slurry so that the sugars can be fermented to produce ethanol. It should be noted that the medial portion 58 of the conduit 16 is constructed such that the volume of the medial portion 58 of the conduit 16 is proportional to the volume of the fermentation chamber 12 and the separation chamber 14 at any given location to insure control of sugar and/or ethanol concentration. Further, the first section 80 of the medial portion 58 of the conduit 16 disposed in the fermentation chamber 12 is constructed of a sufficient size to insure that the alcohol content in the fermentation chamber 12, and the separation chamber 14, does not exceed a concentration of about 20%, the lethal dose of alcohol for the yeast in the yeast slurry. The increased volume of the fermentation chamber 12 from the opposed second end 20 to the first end 18 provides a heat sink for the exothermic reaction of alcohol fermentation and facilitates in the control of the temperature during the fermentation of the mash.

Similarly, the volume of the separation chamber 14 becomes progressively larger from the lower or second end 24 in the direction of the closed end 22 of the separation chamber 14. The increased volume of the upper portion of the separation chamber 14 effectively slows the movement of the beer in the separation chamber 14 as it reaches the upper portion thereof so that suspended yeast and sugars can be more readily separated from the beer and returned to the fermentation chamber 12.

Figure 1A:
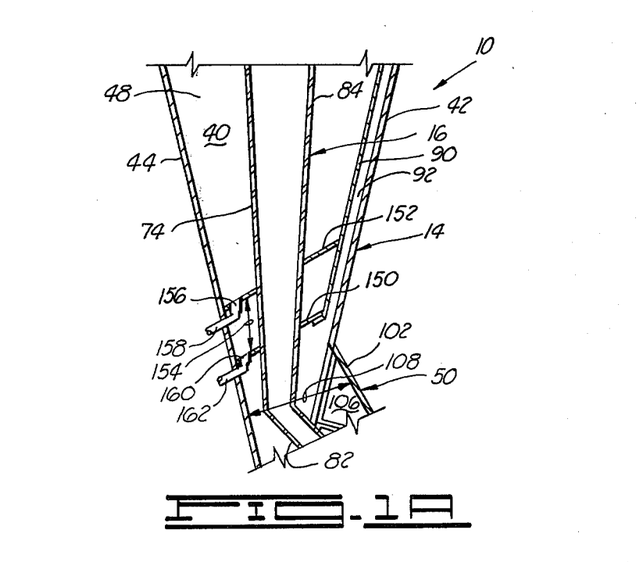
FIG. 1A is a partially broken, cross-sectional view of the separation chamber of the improved fermentation apparatus of the present invention depicting a plurality of filters disposed therein for collecting settled particulate matter in the separation chamber.

Referring now to FIG. 1A, a plurality of filters 150, 152 are angularly disposed across the fluid passageway 48 of the separation chamber 14. The filter 150, depicted as the lowermost filter, is adapted to collect fine particulate materials separating from the beer in the separation chamber 14. The filter 152, a coarser filter, is positioned a distance 154 above the filter 150 and is adapted to collect coarse particulate material separating from the beer in the separation chamber 14 of the fermentation apparatus 10.

The filter 152, which extends across the fluid passageway 48 of the separation chamber 14, is disposed around and connected to the exterior portion of the third section 84 of the conduit 16, and the filter 152 is connected to the first and second sidewalls 38, 40, the rear wall 44 of the separation chamber 14, and the gas separating plate 90. A sump 156 is formed in the filter 152 near the rear wall 44 of the separation chamber 14. The sump 156 fluidly communicates with a conduit 158 so that the particulate matter collected by the filter 150 can be removed from the filter 150, and thus the separation chamber 14 of the fermentation apparatus 10, via the conduit 158.

Figure 4:
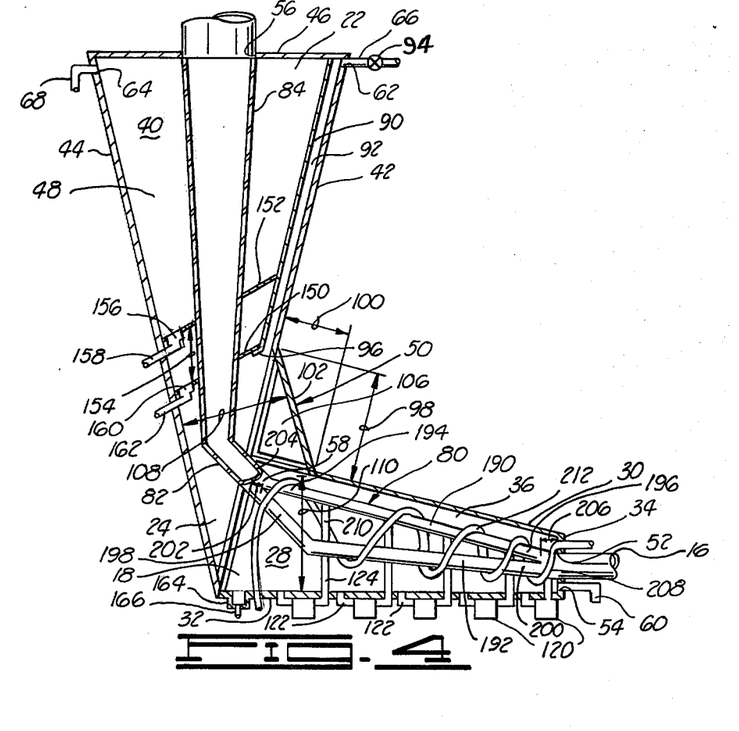
FIG. 4 is a partially broken cross-sectional view of the improved fermentation apparatus of the present invention depicting a pair of filters disposed in the separation chamber for collecting particulate matter in the separation chamber, the portion of the conduit disposed within the fermentation chamber of the apparatus being formed of a plurality of conduit members, and a heat exchange coil disposed around the conduit members for controlling the heat of reaction in the conduits.

The filter 150, which is adapted to remove the finer particulate materials from the beer in the separation chamber 14, and which pass through the filter 152, is disposed across the passageway 48 of the separation chamber 14 in a parallel, spatial relationship with the filter 152. The filter 150 is disposed around the exterior portion of the third section 84 of the conduit 16 and the filter 150 is connected to the first and second side walls 38, 40, the rear wall 44 of the separation chamber 14, and the lower end 96 of the gas separating plate 90 substantially as shown in FIGS. 1A and 4 of the drawings. A sump 160 is formed in the filter 150 at a position near the rear wall 44 of the separation chamber 14. The sump 160 fluidly communicates with a conduit 162 so that particulate materials collected by the filter 150 can be removed from the filter 150, and thus the separation chamber 14 of the fermentation apparatus 10.

The filters 150, 152 can be made of any suitable material which will not contaminate the beer in the separation chamber 14, or poison any suspended yeast and sugar in the beer. Further, the filters 150, 152 are selected of material so that suspended yeast and sugar in the beer which can be separated by gravity therefrom can pass through each of the filters 150, 152 for recirculation into the first section 80 of the medial portion 56 of the conduit 16 via the pumps 120 and the conduits 122, 124.

In order to remove particulate material (i.e., sludge) from the fermentation chamber 12 of the fermentation apparatus 10, and to insure the efficient, effective operation of the fermentation apparatus 10, a sump 164 is formed in the lower wall 44 of the fermentation chamber 12. The sump 164 fluidly communicates with a conduit 166 so that particulate material gathered in the sump 164 can be removed from the fermentation chamber 12 of the fermentation apparatus 10 via the conduit 166.

The flow of the fermentable mash through the conduit 16 of the fermentation apparatus 10 depicted in FIGS. 1, 1A and 4 can be accomplished by any suitable means. For example, a pump (illustrated in FIG. 5) can be operably connected to the conduit 16 so that fermentable mash can be pumped through the conduit 16 at a predetermined rate.

Figure 3:
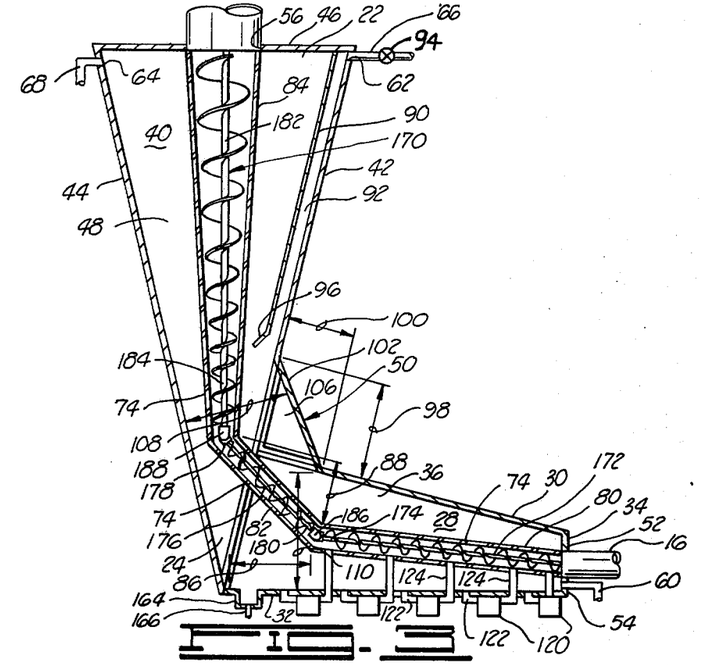
FIG. 3 is a partially broken cross-sectional view of the improved fermentation apparatus of the present invention illustrating an auger disposed within the conduit thereof for moving the fermentable mash through the conduit.

Referring more specifically to FIG. 3, an auger assembly 170 is positioned within the conduit 16, the auger assembly 170 being adapted to move the fermentable mash at a predetermined, constant rate through the conduit 16. The auger assembly 170 comprises a first auger 172 having a first end 174 and a second end (not shown); a second auger 176 having a first end 178 and a second end 180; and a third auger 182 having a first end (not shown) and a second end 184. The first auger 172 is positioned within the conduit 16 and extends through the first section 80 of the medial portion 58 of the conduit 16; the second auger 176 is positioned within the second section 82 of the medial portion 58 of the conduit 16; and the third auger is positioned within the third section 84 of the conduit 16 and extends through the third section 84.

The first end 174 of the first auger 172 is connected to the second end 180 of the second auger 176 via a universal joint 186, and the first end 178 of the second auger 176 is connected to the second end 184 of the third auger 182 via a universal joint 188. The first end (not shown) of the third auger 182 operably communicates with a storage tank (see FIG. 5) for receiving the partially spent mash (known as DDGS, distillers, grains and solubles) from the conduit 16 after the mash has passed through the fermentation chamber 12 and the separation chamber 14. The partially spent mash can be recirculated through the fermentation chamber 12 and the separation chamber 14, or directed to the malting vessel (see FIG. 5) for use in the technique known as back slopping to assist in the pH control of the mash. The second end (not shown) of the first auger 172 operably communicates with a malting vessel (see FIG. 5) so that the fermentable mash can be directed into the conduit 16 and conveyed through the fermentation apparatus 10 via the first, second, and third augers 172, 176 and 182.

Referring now to FIG. 4 the fermentation apparatus 10 of the present invention is illustrated wherein the first section 80 of the medial portion 58 of the conduit 16 comprises a first conduit segment 190 and a spatially disposed second conduit segment 192. The first conduit segment 190 is provided with a first end 194 and a second end 196; and the second conduit segment 192 is provided with a first end 198 and a second end 200. The first ends 194, 198 of the first and second conduit segments 190, 192 are connected together a distance 202 from the open first end 18 of the fermentation chamber such that first and second conduit segments 190, 192 have a common end portion 204 for connection to the second section 82 of the medial portion 58 of the conduit 16. The second ends 196, 200 of the first and second conduit segments 190, 192 are likewise connected together a distance 206 from the end wall 34 of the fermentation chamber 12 such that the first and second conduit segments 190, 192 have a common end portion 208 which extends through the centrally disposed first opening 52 in the end wall 34 of the fermentation chamber 12. Each of the first and second conduit segments 190, 192 are disposed in the fluid passageway 36 of the fermentation chamber 12 such that the first and second conduit segments 190, 192 are upwardly inclined as same extends through the fermentation chamber 12 from the common end portion 208 of the first and second conduit segments 190, 192 to the common end portion 204 of the first and second conduit segments 190, 192 substantially as shown in the drawing. By positioning the first and second conduit segments 190, 192 in an inclined position within the fluid passageway 36 of the fermentation chamber 12 movement of the fermentable mash through the first and second conduit segments 190, 192 is enhanced. Further, by constructing the first section 80 of the medial portion 58 of the conduit 16 from the first and second conduit segments 190, 192, as described, contact between the yeast in the yeast containing slurry in the fermentation chamber 12 and the fermentable sugars in the mash being moved through the fermentation chamber 12 via the first and second conduit segments 190, 192 may be substantially improved.

The first and second conduit segments 190, 192 of the conduit 16 are fluidly permeable such that the yeast containing slurry can be directed into the first and second conduit segments 190, 192 for contact with the mash moving through such conduit segments via the pumps 120 mounted on the lower wall 32 of the fermentation chamber 12. The pumps 120 are, as previously stated, in fluid communication with the aqueous yeast slurry in the fermentation chamber 12 via the conduits 122 and each of the pumps 120 circulate the aqueous yeast slurry to the first conduit segment 190 via the conduit 124. However, since there are two conduit segments 190, 192 forming the first section 80 of the medial portion 58 of the conduit 16, a second conduit 210 directs the yeast containing slurry into the first conduit segment 190. One of each of the second conduits 210 can be disposed between and interconnected to one of the pumps 120 and the second conduit segment 192; or the second conduits 210 can be disposed between the first and second conduit segments 190, 192 to interconnect same so that the yeast containing slurry directed into the first conduit segment 190 (via the pumps 120 and the conduits 122) can thereafter be directed from the first conduit segment 190 to the second conduit segment 192 via the second conduits 210.

In order to control the temperature in the fermentation chamber 12 a cooling coil 212 can be positioned around the first and second conduit segments 190, 192 in a heat exchange relationship. The cooling coil 212 is connected to a cold water source (not shown) so that the desired amount of cold water can be circulated through the cooling coil 212 to extract heat from the first and second conduit segments 190, 192 and thus control the temperature of the yeast slurry in the fermentation chamber 12. Cooling coils are well known in the art and thus no further description of same is believed necessary.

In order to more fully describe the fermentation apparatus 10 of the present invention the operation of the fermentation apparatus will now be set forth with reference to FIG. 5. A grain is employed as the agricultural raw material in the fermentation process illustrated.

When employing a grain, or similar starchy material as the agricultural raw materials for use in the fermentation process, the grain must be ground so that the carbohydrates in the grain are exposed and can be converted through a series of steps into fermentable sugars containing 6 to 12 carbon atoms. The grinding of the grain can be accomplished by the use of a grain mill 220 wherein the grain is ground into a meal which can preferably pass through a 20-mesh screen. However, care should be exercised to insure that the grain is not ground to a consistency of flour or else problems may be encountered in the fermentation of the mash because the mash will become too viscous and difficult to handle.

Once the grain has been ground in the mill 220 to the desired particle size to assure that the carbohydrates in the grain are assessable, an aqueous slurry is prepared by mixing the ground grain directly with water. Stirring of the mixture should prevent the formation of lumps and thus enhance enzyme contact with the starch during the cooking or liquification procedure.

The aqueous slurry of the ground meal is then placed in a cooker 222 wherein the cell walls of the meal are ruptured and the carbohydrates of the meal are converted to complex sugars. The acidity of the slurry should be adjusted during the cooking or liquification process so that the slurry is maintained at a neutral pH. The acidity of the slurry can be adjusted by the addition of dilute basic solutions, e.g., sodium hydroxide, if the pH is too low, or by the addition of concentrated sulfuric acid or lactic acid if the pH of the slurry is too high. In order to convert the carbohydrates of the ground meal in the slurry into the complex sugars an enzyme should be added to the slurry in the proper proportions to insure that the carbohydrates or starch in the meal is completely converted to the complex sugars. Such enzymes are well known in the art and vary in activity. For example, thermophyllic bacterial amylases, which are commercially available, can be added at rates slightly greater than three-quarters of an ounce per bushel of the meal.

Once the enzyme has been added to the slurry the slurry is heated to a sufficient temperature to break the cell walls of the carbohydrates or starch. The rupture of the cell walls, which is caused by heating in hot water, is commonly referred to as gelatinization because the slurry, which is a suspension of insoluble materials in water, is converted to a high viscosity solution. The temperature and pressure at which the cooking or gelatinization of the carbohydrates or starch material in the meal is carried out in the cooker 222 can vary widely. However, under slow cooking conditions and normal atmospheric pressure the gelatinization can be carried out around 60° C.

Once the gelatinization of the carbohydrates or starchy material has occurred, the temperature in the cooker 222 is raised to the optimal temperature for the enzyme employed to convert the starch or carbohydrates to the complex sugars (i.e., soluble dextrins), and the temperature is maintained in the cooker 222 for a period of time effective to enable the enzyme to substantially convert all of the available starch or carbohydrates to the soluble dextrins. Enzymes employed to convert the starch or carbohydrates to the above-mentioned soluble dextrins (i.e., polymeric sugars) are commercially available and are generally most active at a temperature of about 93° C. and require a hold time in the cooker 222 of about two and a half hours if the proper amount of the enzyme is used and all of the carbohydrates are to be converted to the polymeric sugars. Care should be exercised to insure that the starch or carbohydrate conversion by the enzyme is substantially complete prior to subjecting the resulting slurry containing the polymeric sugars to a malting or saccharification process.

After the carbohydrates or starchy materials have been converted to the polymeric sugars as described above, the resulting slurry is introduced into a vessel 224 wherein the malting or saccharification of the polymeric sugars, the soluble dextrins, can be converted to simple sugars containing 6 to 12 carbon atoms. The temperature in the malting or saccharification vessel 224 is lowered to the active range of glucoamylase, an enzyme used for the malting or saccharification of the polymeric sugars, and the pH of the slurry is adjusted to the optimum conversion activity of the glucoamylase. The pH of the slurry is a critical factor which must be carefully controlled because the enzymatic activity ceases when the pH is above 6.5. Glucoamylase is added to the slurry in the proportion required to convert the amount of polymeric sugars available in the mash. It should be noted that the actual amount of the enzyme employed, as well as the temperature at which the malting or saccharification is carried out, will be dependent to a large degree upon the particular enzyme employed.

When the enzyme has been added to the slurry in the malting or saccharification vessel 224, the temperature of the mash is controlled between about 50° C. and 60° C. The mash, as in the cooking process, is continuously stirred during the malting or saccharification to insure intimate contact of the enzyme with the polymeric sugars. Further, the mash should be held at the proper temperature, i.e., between about 50° C. and 60° C., and the pH maintained less than 6.5 until conversion of the polymeric sugars to the simple sugars has been completed.

The product resulting from the before-mentioned milling, cooking and malting or saccharification steps is a fermentable mash which can be converted by the action of a yeast of the genus Saccharomyces into ethanol via the fermentation apparatus 10. The fermentable mash can be directed into the conduit 16 of the fermentation apparatus 10 so that the fermentable mash can be passed through the fermentation apparatus 10 for conversion of the simple sugars in the mash to ethanol. The fermentable mash can be moved through the conduit 16 by any suitable means, such as a pump 226 (or the auger assembly 170 heretofore described with reference to FIG. 3). The simple sugar content of the fermentable mash can vary widely and will be dependent to a large degree upon the particular raw material initially employed as the source for the simple sugars. However, it is generally desirable that the sugar content in the fermentable mash be up to about 30 weight percent.

The fermentation apparatus 10 is filled with an aqueous solution containing a required amount of the yeast. The amount of yeast in the fermentation apparatus 10 can vary widely and is well known in the art of fermentation. Further, the amount of the yeast required will vary depending to a large degree upon the particular strain of the yeast used to ferment the simple sugars in the fermentable mash. The yeast can be added to the fermentation apparatus 10 in a dry state, or the yeast can be mixed with water and supplied to the fermentation apparatus 10.

Once the desired amount of yeast has been disposed in the fermentation apparatus 10, the fermentation apparatus 10 filled with water to provide a resulting yeast-containing slurry having the desired amount of yeast, and the fermentable mash in the conduit 16 is being moved through the conduit 16 and the fermentation apparatus 10, beer will be formed in the fermentation apparatus 10. The beer so formed is continuously withdrawn from the fermentation apparatus 10 via conduit 68 and placed in a storage tank 228.

In order to maintain a proper liquid level in the fermentation apparatus 10, water is supplied to the fermentation apparatus 10 from a water storage vessel 230 via conduit 60 at a rate equal to the rate of withdrawal of the beer from the fermentation apparatus 10 via the conduit 68. The mash being moved through the conduit 16 is moved through the conduit 16 at a rate sufficient to enable the yeast to react with the simple sugars of the mash and produce a beer solution containing about 10% ethanol. The partially spent mash in the conduit 16, upon exiting the fermentation apparatus 10, is carried via the conduit 16 to a storage tank 232.

The partially spent mash can also be directed, via a conduit 234, to the malting or saccharification vessel 224 and employed in the process known as "back slopping" to control the pH of the slurry in the malting or saccharification vessel 224.

The temperature at which the fermentation of the simple sugars is carried out in the fermentation apparatus 10 and the pH of the yeast containing slurry greatly affect the ethanol production in the fermentation apparatus 10. Yeasts used in the ethanol production which are members of the genus Saccharomyces are most effective in pH ranges between 3.0 and 5.0, and at temperatures between 27° C. and 35° C. Thus, care must be exercised to ensure that the fermentation apparatus 10 is maintained at the before-mentioned temperature and the pH of the yeast-containing aqueous slurry employed in the fermentation apparatus 10 is maintained at the proper pH level.

The carbon dioxide gas generated during the fermentation of the simple sugars in the fermentation apparatus 10 are controllably withdrawn from the apparatus 10 via the conduit 66 as heretofore described. It should be noted that the conduit 66 is positioned above the liquid level of the beer in the fermentation apparatus 10, and the construction of the fermentation apparatus 10 prevents the carbon dioxide from entering the separation chamber portion of the fermentation apparatus 10 and agitating the beer.

It is clear that the present invention is well adapted to carry out the objects and attain the ends and advantages mentioned as well as those inherent therein. While a presently preferred embodiment of the invention has been described for purposes of this disclosure, numerous changes may be made which will readily suggest themselves to those skilled in the art and which are encompassed within the spirit of the invention disclosed and as defined in the appended claims.

What is claimed is:

1. A fermentation apparatus for continuous fermentation of a sugar containing material to produce beer, the fermentation apparatus comprising:
   a substantially horizontally disposed fermentation chamber having a first end and a second end;
   a substantially vertically disposed separation chamber having an upper end and a lower end, the lower end of the separation chamber connected to the first end of the fermentation chamber such that the separation chamber is in fluid communication with the fermentation chamber;
   mash directing means disposed in the fermentation chamber and the separation chamber, having a first end adjacent the second end of the fermentation chamber and having a second end adjacent the upper end of the separation chamber, for directing mash introduced at the first end through the fermentation chamber and out of the fermentation chamber adjacent its second end, and for directing such mash into the separation chamber adjacent its lower end, and for directing such mash through the separation chamber and out the separation chamber at the second end of the mash directing means, the mash directing means being adapted to retain the mash therein;
   mash transporter means for powering movement of mash from the first end to the second end of the mash directing means;
   circulating means for circulating a yeast-containing slurry in the fermentation chamber into contact with the mash in the mash directing means; and
   gas separating means positioned within the separation chamber for collecting gases generated by fermentation of the mash and separating such gases from the beer so produced.

2. The continuous fermentation apparatus of claim 1 wherein the fermentation chamber comprises:
   a first side wall;
   a second side wall;
   an upper wall;
   a lower wall; and
   an end wall having an opening therein, the opening adapted to receive the mash directing means, each of the walls being connected to the end wall and to the adjacently disposed walls to form a fluid passageway therebetween, the first side wall, the second side wall, and the upper wall diverging from the end wall of the fermentation chamber such that the rate of flow of the yeast slurry through the fluid passageway of the fermentation chamber decreases as a function of the distance from the first end to the second end of the fermentation chamber.

3. The continuous fermentation apparatus of claim 2 wherein the separation chamber comprises:
   a first side wall;
   a second side wall;
   an upper wall;
   a lower wall; and
   an end wall having an opening therein, the opening adapted to receive the mash directing means, each of the walls being connected to the end wall and to the adjacently disposed walls to form a fluid passageway therebetween, the front wall, the rear wall, the first side wall, and the second side wall converging from the end wall such that the rate of flow of the fermentation liquid through the fluid flow passageway of the separation chamber decreases as a function of the distance from the second end of the separation chamber to the first end of the separation chamber.

4. The continuous fermentation apparatus of claim 3 wherein the upper wall of the fermentation chamber terminates a distance from the first end of the fermentation chamber, the front wall of the separation chamber terminates a distance from the second end of the separation chamber and the front wall of the separation chamber is positioned in an offset relation with the upper wall of the fermentation chamber, and wherein the fermentation apparatus further comprises:
   connecting means for connecting the upper wall of the fermentation chamber to the front wall of the separation chamber such that the distance between the connecting means and an oppositely disposed portion of the back wall of the separation chamber substantially corresponds to the distance between the upper wall and an oppositely disposed portion of the lower wall of the fermentation chamber.

5. The continuous fermentation apparatus of claim 4 which further comprises:
first conduit means disposed through the front wall of the separation chamber and fluidly communicating with an upper portion of the separation chamber; and
channel forming means positioned in the separation chamber and extending a distance along the front wall of the separation chamber, the channel forming means cooperating with the front wall of the separation chamber to form a channel for directing gases generated during fermentation of the mash to the first conduit means of the separation chamber.

6. The continuous fermentation aparatus of claim 5 which further comprises:
second conduit means disposed through the rear wall of the separation chamber and fluidly communicating with the separation chamber for removing the beer from the separation chamber.

7. The continuous fermentation apparatus of claim 5 wherein the channel forming means comprises:
a plate having an upper end and a lower end, the upper end of the plate being connected to the end wall of the separation chamber, the plate extending from the end wall at a position between the first and second walls such that the plate cooperates with the front wall of the separation chamber to provide the channel therebetween.

8. The continuous fermentation apparatus of claim 7 wherein the lower end of the plate of the channel forming means is disposed substantially opposite a lower end of the front wall of the separation chamber, the lower end of the plate having a flared portion thereon which is flared in a direction away from the front wall of the separation chamber, the flared lower end of the plate cooperating with the connecting means to form a funnel shaped inlet into the channel formed between the plate and the front wall of the separation chamber.

9. The continuous fermentation apparatus of claim 8 which further comprises:
a first filter means for removing particulate matter from the separation chamber, the first filter means being positioned in the separation chamber between the flared lower end of the plate of the channel forming means and the rear wall of the separation chamber, the first filter means being disposed in an angular relationship such that the portion of the first filter means adjacent the back wall of the separation chamber is disposed a distance below the portion of the first filter means adjacent the flared lower end of the plate member of the channel forming means; and
a slump means formed in the first filter means at a position substantially adjacent the rear wall of the separation chamber for removing the particulate matter from the first filter means.

10. The continuous fermentation apparatus of claim 9 which further comprises:
a second filter means for removing particulate matter from the separation chamber, the second filter means being positioned in the separation chamber in a substantially parallel, spatial relationship with the first filter means, the second filter means being disposed across the separation chamber between the plate of the channel forming means and the rear wall of the separation chamber; and
a sump formed in the second filter means at a position substantially adjacent the rear wall of the separation chamber for removing particulate matter from the second filter means.

11. The continuous fermentation apparatus of claim 1 wherein the circulating means comprises at least one pump assembly having an inlet and an outlet, the inlet of the pump assembly fluidly communicating with the yeast-containing slurry in the fermentation chamber, the outlet of the pump fluidly communicating with the mash in the mash directing means so that the yeast-containing slurry can be directed into the mash directing means for contact with the mash.

12. The continuous fermentation apparatus of claim 1 which further comprises a sump formed in the open first end of the fermentation chamber, the sump adapted to collect and remove sediment formed during the fermentation of the mash with the yeast-containing slurry in the fermentation chamber.

13. The continuous fermentation apparatus of claim 1 wherein the mash directing means disposed in the fermentation chamber comprises a first and second conduit segment, the first and second conduit segments being operably connected to the circulating means such that the yeast-containing slurry can be passed through the mash in each of the first and second conduit segments.

14. The fermentation apparatus of claim 13 which further comprises:
heat exchange means disposed about the first and second conduit segments in the fermentation chamber for controlling the temperature of the yeast-containing slurry in the fermentation chamber.

15. The continuous fermentation apparatus of claim 1 in which the mash transporter means further comprises:
auger means disposed within and extending throughout the mash directing means for moving the mash at a constant rate through the mash conveying means.

16. The continuous fermentation apparatus of claim 1 wherein the mash directing means comprises a conduit having a first end portion, a medial portion, and a second end portion, the medial portion of the conduit being disposed in the fermentation chamber and the separation chamber, the medial portion of the conduit being fluid permeable such that upon circulating the yeast-containing slurry in the fermentation chamber, the yeast-containing slurry can flow through the fluid permeable medial portion of the conduit and into contact with the mash transported therethrough.

17. The continuous fermentation apparatus of claim 1 which further comprises valve means operably connected to the first conduit means of the separation chamber for controlling the rate of flow of the gases generated during the fermentation of the mash in the fermentation chamber from the apparatus via the first conduit means of the separation chamber.

18. A continuous fermentation apparatus comprising:
a fermentation chamber having an open first end, a closed second end, and a liquid inlet for introducing liquid into the fermentation chamber;
a separation chamber having a closed upper first end, an open lower second end, a first outlet and a second outlet, the open second end of the separation chamber operably connected to the first open end of the fermentation chamber and establishing fluid communication therebetween;

a conduit including means for transporting mash through the fermentation chamber and the separation chamber, the conduit having a first end, a medial portion, and a second end, the second end of the conduit extending through the closed first end of the separation chamber and connected thereto in a fluid-tight relationship, the first end of the conduit extending through the closed second end of the fermentation chamber and connected thereto in a fluid-tight relationship, and the medial portion of the conduit extending through the fermentation chamber and the separation; chamber; and circulating means operably connected to the fermentation chamber for circulating a yeast-containing slurry in the fermentation chamber into contact with the mash in the medial portion of the conduit.

19. The continuous fermentation apparatus of claim 18 wherein the fermentation chamber comprises:

a first side wall;

a spatially disposed second side wall;

an upper wall;

a spatially disposed lower wall; and an end wall having an opening therein, the opening adapted to receive the second end of the conduit, each of the walls being connected to the end wall and each adjacently disposed wall to form a fluid passageway therebetween, the first side wall, the second side wall, and the upper wall diverging from the end wall of the fermentation chamber such that the rate of flow of the yeast slurry through the fluid passageway of the fermentation chamber descreases as a function of the distance from the first end to the second end of the fermentation chamber.

20. The continuous fermentation apparatus of claim 19 wherein the separation chamber comprises:

a first side wall;

a second side wall;

a front wall;

a rear wall; and an end wall having an opening therein, the opening adapted to receive the first end of the conduit, each of the walls being connected to the end wall and to the adjacently disposed walls to form a fluid passageway therebetween, the front wall, the rear wall, the first side wall, and the second side wall converging from the end wall such that the rate of flow of the liquid through the fluid flow passageway of the separation chamber decreases as a function of the distance from the second end of the separation chamber to the first end of the separation chamber.

21. The continuous fermentation apparatus of claim 20 wherein the upper wall of the fermentation chamber terminates a distance from the first end of the fermentation chamber, the front wall of the separation chamber terminates a distance from the second end of the separation chamber and the front wall of the separation chamber is positioned in an offset relation with the upper wall of the fermentation chamber, and wherein the fermentation apparatus further comprises:

connecting means for connecting the upper wall of the fermentation chamber to the front wall of the separation chamber such that the distance between the connecting means and the opposed portion of the back wall of the separation chamber substantially corresponds to the distance between the upper wall and the opposed portion of the lower wall of the fermentation chamber at the position of attachment of the connecting means to the upper wall.

22. The continuous fermentation apparatus of claim 21 which further comprises:

channel forming means disposed in the separation chamber and extending a distance along the front wall of the separation chamber, the channel forming means cooperating with the front wall of the separation chamber to direct gases generated during fermentation of the mash in the fermentation chamber to the first outlet of the separation chamber.

23. The continuous fermentation apparatus of claim 22 wherein the channel forming means comprises:

a plate having an upper end and a lower end, the upper end of the plate being connected to the end wall of the separation chamber such that the plate extends between the first and second walls of the separation chamber, the plate cooperating with the front wall of the separation chamber to provide a channel therebetween so that gas generated in the fermentation chamber by fermentation of the mash can be directed into the channel for exiting the apparatus via the first outlet disposed in the separation chamber.

24. The continuous fermentation apparatus of claim 23 wherein the lower end of the plate of the channel forming means is substantially aligned with a lower end of the front wall of the separation chamber, and the lower end of the plate is flared in a direction away from the front wall of the separation chamber, the flared lower end of the plate cooperating with the connecting means to form a funnel shaped inlet into the channel formed between the plate and the front wall of the separation chamber.

25. The continuous fermentation apparatus of claim 23 which further comprises:

a first filter means angularly positioned in the separation chamber for removing particulate matter from the separation chamber, the first filter means being positioned in the separation chamber between the flared lower end of the plate of the channel forming means and the back wall of the separation chamber; and sump means formed in the first filter means for removing particulate matter from the first filter means.

26. The continuous fermentation apparatus of claim 25 which further comprises:

a second filter means for removing particulate matter from the separation chamber, the second filter means being positioned in the separation chamber in a substantially parallel, spatial relationship with the first filter means; and sump means formed in the second filter means for removing particulate matter from the second filter means.

27. The continuous fermentation apparatus of claim 18 wherein the circulating means comprises a plurality of pump assemblies, each of the pump assemblies having an inlet and an outlet, the inlet of each of the pump assemblies communicating with the yeast-containing slurry in the fermentation chamber, the outlet of each of the pump assemblies fluidly communicating with the mash in the medial portion of the conduit.

28. The continuous fermentation apparatus of claim 18 which further comprises a sump means formed in the lower wall of the fermentation chamber for collecting sediment formed during the fermentation of the mash with the yeast-containing slurry in the fermentation chamber.

29. The continuous fermentation apparatus of claim 18 wherein the medial portion of the conduit disposed in the fermentation chamber comprises a first and second conduit segment, the first and second conduit segments being operably connected to the circulating means such that the yeast-containing slurry can be passed through the mash in each of the first and second conduit segments.

30. The fermentation apparatus of claim 29 which further comprises:
heat exchange means disposed about the first and second conduit segments in the fermentation chamber and in a heat exchange relationship therewith for controlling the temperature of the yeast-containing slurry in the fermentation chamber.

31. The continuous fermentation apparatus of claim 18 wherein the means for transporting mash comprises:
auger means disposed within and extending throughout the conduit for moving the mash at a constant rate through the conduit when the auger means is operatively activated.

32. The continuous fermentation apparatus of claim 18 wherein the medial portion of the conduit is formed of a fluid permeable material such that upon circulation of the yeast-containing slurry in the fermentation chamber, the yeast containing slurry can enter and exit the fluid permeable conduit for contact with the mash moving therethrough.

33. The continuous fermentation apparatus of claim 18 which further comprises valve means operably disposed in the first outlet of the separation chamber for controlling the rate of flow of the gases generated during the fermentation of the mash in the fermentation chamber from the apparatus via the first outlet of the separation chamber.

* * * * *

UNITED STATES PATENT AND TRADEMARK OFFICE
CERTIFICATE OF CORRECTION

PATENT NO. : 4,298,693
DATED : November 3, 1981
INVENTOR(S) : Michael W. Wallace It is certified that error appears in the above-identified patent and that said Letters Patent are hereby corrected as shown below:

Column 15, line 58, the word "slump" should be --sump--.

Signed and Sealed this

Thirteenth Day of April 1982

|SEAL|

Attest:

GERALD J. MOSSINGHOFF

Attesting Officer     Commissioner of Patents and Trademarks